United States Patent
Theze et al.

(10) Patent No.: US 10,894,035 B2
(45) Date of Patent: Jan. 19, 2021

(54) USE OF INDOLE COMPOUNDS TO STIMULATE THE IMMUNE SYSTEM

(71) Applicant: DIACCURATE, Paris (FR)

(72) Inventors: Jacques Theze, Paris (FR); Blanche Tamarit, Paris (FR)

(73) Assignee: DIACCURATE, Paris (FR)

( * ) Notice: Subject to any disclaimer, the term of this patent is extended or adjusted under 35 U.S.C. 154(b) by 0 days.

(21) Appl. No.: 15/755,587

(22) PCT Filed: Aug. 30, 2016

(86) PCT No.: PCT/EP2016/070367
§ 371 (c)(1),
(2) Date: Feb. 27, 2018

(87) PCT Pub. No.: WO2017/037041
PCT Pub. Date: Mar. 9, 2017

(65) Prior Publication Data
US 2018/0344694 A1 Dec. 6, 2018

(30) Foreign Application Priority Data
Aug. 31, 2015 (EP) .................................... 15306333

(51) Int. Cl.
*A61K 31/404* (2006.01)
*A61K 45/06* (2006.01)
*A61P 31/18* (2006.01)

(52) U.S. Cl.
CPC ............ *A61K 31/404* (2013.01); *A61K 45/06* (2013.01); *A61P 31/18* (2018.01)

(58) Field of Classification Search
CPC .............................. A61K 31/18; A61K 31/404
See application file for complete search history.

(56) References Cited

U.S. PATENT DOCUMENTS

| | | | |
|---|---|---|---|
| 2004/0110825 A1* | 6/2004 | Loh .................... | A61K 31/00 514/419 |
| 2009/0062369 A1* | 3/2009 | Trias .................... | A61K 31/404 514/419 |
| 2016/0311926 A1 | 10/2016 | Theze et al. | |
| 2018/0296632 A1 | 10/2018 | Tamarit et al. | |

FOREIGN PATENT DOCUMENTS

| | | | | |
|---|---|---|---|---|
| WO | WO-2010081022 A1 * | 7/2010 | ............. | A61K 31/44 |
| WO | WO-2012055814 A1 * | 5/2012 | ............. | A61K 31/00 |
| WO | WO 2015/097140 | 7/2015 | | |
| WO | WO 2019/166412 | 9/2019 | | |
| WO | WO 2019/166413 | 9/2019 | | |
| WO | WO 2019/166664 | 9/2019 | | |
| WO | WO 2019/166665 | 9/2019 | | |

OTHER PUBLICATIONS

Post et al., Q J Med, 1996;89:505-508. (Year: 1996).*

(Continued)

*Primary Examiner* — San Ming R Hui
(74) *Attorney, Agent, or Firm* — Saliwanchik, Lloyd & Eisenschenk

(57) ABSTRACT

Methods for treating immunodeficiencies are provided using indole-based compounds.

10 Claims, 2 Drawing Sheets

Concentration in Compound B (µM)

(56) References Cited

OTHER PUBLICATIONS

Matsumoto, Y. et al. "Antiviral Activity of Glycyrrhizin against Hepatitis C Virus In Vitro" *PLoS One*, Jul. 18, 2013, pp. 1-10, vol. 8, No. 7.

Pubchem database [Online] Accession No. AID 158925, "Inhibition of Recombinant Human Secretory Phospholipase A2 (SPLA2), Chromogenic Screening Assay" Aug. 24, 2014, pp. 1-8.

Smart, B. P. et al. "Inhibition of the complete set of mammalian secreted phospholipases $A_2$ by indole analogues: a structure-guided study" *Bioorganic & Medicinal Chemistry*, Apr. 1, 2004, pp. 1737-1749, vol. 12.

Tomita, Y. et al. "Effect of a Selective Inhibitor of Secretory Phospholipase $A_2$, S-5920/LY315920Na, on Experimental Acute Pancreatitis in Rats" *Journal of Pharmacological Sciences*, Jan. 1, 2004, pp. 144-154, vol. 96, No. 2.

Written Opinion in International Application No. PCT/EP2016/070367, dated Nov. 9, 2016, pp. 1-6.

Bradley, J.D. et al. "A Randomized, Double-Blinded, Placebo-Controlled Clinical Trial of LY333013, a Selective inhibitor of Group II Secretory Phospholipase $A_2$, in the Treatment of Rheumatoid Arthritis." *The Journal of Rheumatology*, 2005, pp. 417-423, vol. 32, No. 3.

Snyder, D.W. et al. "Pharmacology of LY315920/S-5920,[1] [[3-(Aminooxoacetyl)-2-ethyl-1-(phenylmethyl)-1H-indol-4-yl]oxy]acetate, a Potent and Selective Secretory Phospholipase $A_2$ Inhibitor: A New Class of Anti-Inflammatory Drugs, SPI" *The Journal of Pharmacology and Experimental Therapeutics*, 1999, pp. 1117-1124, vol. 288, No. 3.

Currently pending claims of U.S. Appl. No. 16/976,086, filed Aug. 27, 2020, pp. 1-3.

Currently pending claims of U.S. Appl. No. 16/976,088, filed Aug. 27, 2020, pp. 1-3.

Currently pending claims of U.S. Appl. No. 16/976,485, filed Aug. 28, 2020, pp. 1-3.

Currently pending claims of U.S. Appl. No. 16/976,486, filed Aug. 28, 2020, pp. 1-3.

\* cited by examiner

USE OF INDOLE COMPOUNDS TO STIMULATE THE IMMUNE SYSTEM

CROSS-REFERENCE TO RELATED APPLICATION

This application is the U.S. national stage application of International Patent Application No. PCT/EP2016/070367, filed Aug. 30, 2016.

FIELD OF THE INVENTION

The present invention relates to compositions and methods to induce or stimulate an immune response in a subject using particular indole-based compounds. The invention is particularly effective for stimulating CD4 T cells and may be used to treat HIV infected patients.

INTRODUCTION

CD4 T lymphocytes play a pre-eminent role in controlling the immune system (both cellular and humoral responses) and are critical in various disease conditions such as cancer or infectious diseases.

During the immunological disease associated with HIV pathogenesis, less than 0.5% of all CD4 T cells are actually infected (as measured in the peripheral blood), but the great majority of CD4 T cells shows major regulatory dysfunction. Uninfected CD4 T lymphocytes progressively lose their function, become anergic, and their numbers decrease resulting in CD4 lymphopenia. Anergy and lymphopenia are the hallmarks of the immunodeficiency characterizing HIV-infected patients. The mechanisms behind these phenomena have never been fully elucidated (1). Immune activation and inflammation also play a critical role in HIV pathogenesis (2, 3).

The inventors have previously reported the identification, isolation and characterization, from human plasma, of the protein responsible for this aberrant state of CD4 T cell activation, designated sPLA2G1B (WO2015/097140).

The present invention relates to the use of a particular class of sPLA2G1B inhibitory compounds to stimulate the immune system in a subject in need thereof. More particularly, the inventors have selected a particular group of indole-based compounds that exhibit potent sPLA2G1B inhibitory effect with a suitable specificity profile. The inventors have demonstrated that these compounds are able to completely neutralize the capacity of sera from viremic HIV-infected patients to induce abnormal and pathogenic responses in the CD4 lymphocytes purified from healthy donors, and thus to restore CD4 T cell function in HIV infected subjects.

SUMMARY OF THE INVENTION

An object of the invention relates to a method for stimulating or inducing an immune response in a subject, comprising exposing the subject to a compound of formula A, or a salt, ester, hydrate, racemate, enantiomer, prodrug or metabolite thereof.

A further object of the invention relates to a method of treatment of an immunodeficiency disorder in a subject, comprising exposing the subject to a compound of formula A, or a salt, ester, hydrate, racemate, enantiomer, prodrug or metabolite thereof.

Another object of the invention relates to the use of a compound of formula A, or a salt, ester, hydrate, racemate, enantiomer, prodrug or metabolite thereof, for the manufacture of a medicament for inducing or stimulating an immune response or for treating an immunodeficiency disorder in a subject.

Another object of the invention relates to a compound of formula A, or a salt, ester, hydrate, racemate, enantiomer, prodrug or metabolite thereof, for use in a method of inducing or stimulating an immune response or of treating an immunodeficiency disorder in a subject.

The invention is particularly suited to treat immunodeficient subjects or subject in need of stimulated immunity (e.g., subjects having an infectious disease or a cancer). In this regard, a particular object of the invention resides in a method of treating an infectious disease in a subject, comprising administering to the subject a compound of formula A or a salt, ester, hydrate, racemate, enantiomer, prodrug or metabolite thereof.

A more particular embodiment of the invention relates to a method of treating AIDS in a HIV-infected subject, comprising administering to the subject a compound of formula A or a salt, ester, hydrate, racemate, enantiomer, prodrug or metabolite thereof.

In another aspect, the invention relates to a pharmaceutical composition comprising (i) a compound of formula A, or a salt, ether, hydrate, racemate, enantiomer, prodrug or metabolite thereof and (ii) a further antiviral or anticancer agent.

The invention may be used in any mammal, including humans and non-human animals such as, without limitation, domesticated animals (e.g., cows, sheep, cats, dogs, and horses), non-human primates (such as monkeys), rabbits, and rodents (e.g., mice and rats). It is particularly suited for use in human subjects. It may be used to increase the immune response in any mammal, and it is particularly adapted to induce potent CD4-T cell activity in immunodepressed subjects.

DETAILED DESCRIPTION OF THE INVENTION

Figure 1:
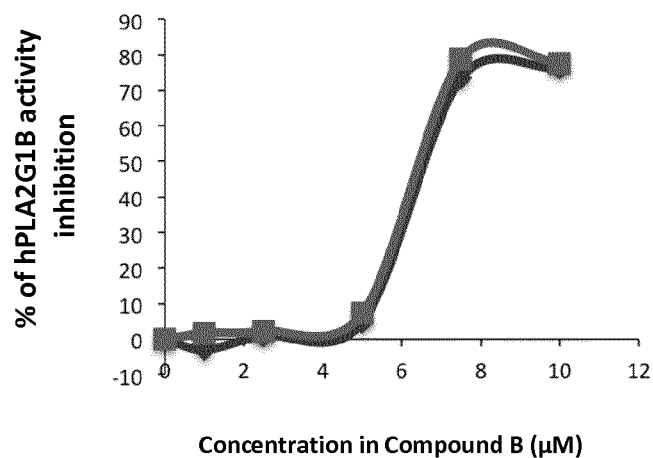
FIG. 1: Compound B inhibits sPLA2G1B: Recombinant PLA2G1B (75 nanoM) was first exposed 30 mn to indicated concentrations of compound B. The mixture was then applied in the bioassay described in Materials and Methods. % inhibition of IL-7-induced nuclear translocation of phospho STAT5 was measured by STED microscopy.

The present invention relates to compositions and methods for modulating the immune system in a subject in need thereof. The invention more particularly provides compositions and methods for stimulating the immune response or system, particularly in immunodepressed or immunodefective subjects.

The present invention discloses the remarkable capacity of particular indole-based compounds to completely neutralize sPLA2G1B-mediated abnormal and pathogenic CD4 T lymphocytes. Remarkably, the effect of these compounds was found to be even more potent on sPLA2G1B present in the plasma of patients than on the recombinant enzyme contained in serum free buffer. Such compounds thus represent novel and potent agents for stimulating the immune system in human subjects and, more particularly, for treating HIV-infected patients. Administered early during the infection process, they can prevent evolution towards an immune disease and prevent appearance of the immune deficiency. Given later, for instance in conjunction with Highly Active Anti-Retroviral Therapy (HAART), they facilitate the recovery of a functional immune system leading to a control of HIV infection by the immune system.

An object of the invention thus relates to a method for stimulating or inducing an immune response in a subject, comprising exposing the subject to a compound of formula A, or a salt, ester, hydrate, racemate, enantiomer, prodrug or metabolite thereof.

A further object of the invention relates to a method of treatment of an immunodeficiency disorder in a subject, comprising exposing the subject to a compound of formula A, or a salt, esther, hydrate, racemate, enantiomer, prodrug or metabolite thereof.

Another object of the invention relates to the use of a compound of formula A, or a salt, ester, hydrate, racemate, enantiomer, prodrug or metabolite thereof, for the manufacture of a medicament for inducing or stimulating an immune response or for treating an immunodeficiency disorder in a subject.

The invention also relates to the use of compounds of formula A for stimulating or restoring CD4 T cells in a subject.

Compounds of formula A designate compounds having the following structure A:

wherein:
each X is independently an oxygen or sulfur atom, preferably an oxygen atom;
$R^1$ is $(CH_2)_n$—Ar wherein n is 0, 1 or 2 and Ar is a $C_5$-$C_7$ aromatic group, preferably a phenyl group,
$R^2$ is a $C_1$-$C_4$ alkyl, preferably ethyl; and
$R^3$ is $(O)_m$—$(CH_2)_p$—$COOR^4$ wherein m is 0 or 1, preferably 1; p is 0, 1, or 2, preferably 1; and $R^4$ is a hydrogen atom or a $C_1$-$C_3$ alkyl.

Compounds of formula A have been proposed in the literature for treating metabolic disorders and coronary diseases (see e.g. WO2010/081022 or WO2012/027529). However, their effect on the immune system, particularly CD4 T lymphocytes, had never been suggested and their ability to completely neutralize sPLA2GIB-mediated CD4 anergy in HIV infected subjects was totally unknown.

In a preferred embodiment, the compounds for use in the invention are compounds of formula A wherein:
each X is an oxygen; and/or
$R^1$ is —$(CH_2)$—Ar wherein Ar is a C5-C7 aromatic group, preferably a phenyl group, and/or
R2 is a C1-C3 alkyl, preferably ethyl; and/or
R3 is —O—$(CH_2)_p$—$COOR^4$ wherein p is 0, 1 or 2, preferably 1, and $R^4$ is a hydrogen atom or a C1-C3 alkyl.

In a further preferred embodiment, the compounds for use in the invention are compounds of formula A wherein:
each X is an oxygen; and
$R^1$ is —$(CH_2)$—Ar wherein Ar is a phenyl group, and
$R^2$ is ethyl; and
$R^3$ is —O—$(CH_2)$—$COOR^4$ wherein R4 is a hydrogen atom or a methyl group.

In a most preferred embodiment, the compound is 3-(2-amino-1,2-dioxoethyl)-2-ethyl-1-(phenylmethyl)-1H-indol-4-yl)oxy)acetic acid (compound B) or a pharmaceutically acceptable salt, hydrate, or prodrug thereof. The structure of compound B is represented below:

Compound B

Compounds of formula A may be produced according to methods known per se in the art, as illustrated for instance in WO2010/081022 or WO2012/027529.

The term "salt" refers to any pharmaceutically acceptable inorganic or organic acid/basic addition salt of a compound of the present invention. Pharmaceutically acceptable acid salts according to the invention include, without limitation, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable basic salts of the invention include, without limitation, sodium, potassium, calcium, magnesium, ammonium, or choline salts.

The term "prodrug" as used herein refers to any functional precursor of a compound of structure A which, when administered to a biological system, generates said compound as a result of e.g., spontaneous chemical, enzymatic, biological and/or metabolic reaction(s). Typical prodrugs have the structure Y-A wherein Y is a protective group and is cleaved from the prodrug in vivo to release compound A. Prodrugs are usually inactive or less active than the resulting drug and can be used, for example, to improve the physicochemical or pharmacokinetic properties of a compound.

The term "metabolite" designates a molecule which results from the in vivo modification or processing of a compound A after administration to an organism. Such modifications may occur through specialized enzymatic systems leading to molecules retaining a biological activity of the compound.

The term "enantiomer" refers to isolated optically pure enantiomers, as opposed to a mixture (at any relative ratio) of isomers. Compounds for use in the invention may thus be optically pure enantiomers or any mixtures (e.g., racemate) thereof.

Compositions

The compounds for use according to the invention may be formulated with any pharmaceutically acceptable excipient, vehicle or carrier. They may be in the form of ointment, gel, paste, liquid solutions, suspensions, tablets, gelatin capsules, capsules, suppository, powders, nasal drops, or aerosol, preferably in the form of an injectable solution or suspension. For injections, the compounds are generally packaged in the form of liquid suspensions, which may be injected via syringes or perfusions, for example. In this respect, the compounds are generally dissolved in saline, physiological, isotonic or buffered solutions, compatible with pharmaceutical use and known to the person skilled in the art. Thus, the compositions may contain one or more agents or excipients selected from dispersants, solubilizers, stabilizers, preservatives, etc. Agents or excipients that can be used in liquid and/or injectable formulations are notably methylcellulose, hydroxymethylcellulose, carboxymethylcellulose, polysorbate 80, mannitol, gelatin, lactose, vegetable oils, acacia, etc. The carrier can also be selected for example from methyl-beta-cyclodextrin, a polymer of acrylic acid (such as carbopol), a mixture of polyethylene glycol and polypropylene glycol, monoetrhanol amine and hydroxymethyl cellulose.

The compositions generally comprise an effective amount of a compound of formula A, e.g., an amount that is effective to inhibit sPLA2G1B. Generally, the compositions according to the invention comprise from about 0.01 µg to 1000 mg of a compound of formula A, for example between 0.05 µg and 600 mg, preferably between 0.05 µg and 500 mg, for example between 5 mg and 500 mg. The dosages may be adjusted by the skilled person depending on the disease and subject. A particular dosage for compound B is comprised between 50 mg and 500 mg.

The compositions of the invention can further comprise one or more additional active compounds, for simultaneous or sequential use. In particular, compounds A may be used in combination with further anti-viral agents such as anti-retroviral agents.

The invention also relates to a pharmaceutical composition comprising a compound of formula A as defined above, a further antiviral agent and, optionally, a pharmaceutically acceptable excipient. The compositions of the invention may be formulated into any suitable device or container such as syringe, ampoule, flask, bottle, pouch, etc.

The invention also relates to a kit comprising (i) a container comprising a compound of formula A as previously described, (ii) a container comprising a further antiviral agent, and optionally (iii) written instructions for using the kit.

Diseases

The compounds and compositions of the invention may be used to treat any disease related to an inappropriate (e.g., defective or improper) immune response, particularly to an inappropriate CD4 T cell activity, as well as any disease where an increased immunity may ameliorate the subject condition. These diseases are sometime referred to as "immune disorders" or "immunodeficiencies" in the present application. This includes particularly immunodefective situations caused by viral infection or pathogenic infection, or cancers.

As used herein, the term "treatment" or "treat" refers for instance to any clinical intervention in an attempt to alter the natural course of the individual being treated, and can be performed either for preventive or curative purpose. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions and methods of the invention are used to delay development of a disease or disorder or to slow the progression of a disease or disorder.

Examples of diseases that can benefit from such treatment are all diseases with an immunodeficiency such as HIV-mediated immunodeficiency. In this regard, in a particular embodiment, the invention is directed to methods for treating an immunodeficiency or an associated disorder in a subject in need thereof, comprising administering a compound of formula A to said subject.

In another particular embodiment, the invention is directed to a compound of formula A for use for treating an immunodeficiency or an associated disorder in a subject in need thereof.

Immunodeficiencies and associated disorders designate any condition or pathology characterized by and/or caused by a reduced immune function or response in a subject. Immunodeficiencies may be caused by e.g., viral infection (e.g., HIV, hepatitis B, etc.), bacterial infection, cancer, or other pathological conditions. The term "immunodeficiency-associated disorder" therefore designates any disease caused by or associated with an immunodeficiency. The invention is particularly suitable for treating immunodeficiencies related to CD4-T cells, and associated diseases.

In a particular embodiment, the invention relates to methods of treating HIV infection in a subject by administering a compound of formula A to said subject. In some embodiments the subject is an early HIV patient and the methods results in increasing the probability that the patient is a HIV controller. In some embodiments the subject is a patient with low immunoreconstitution after antiretroviral treatment and/or with severe idiopathic CD4 T lymphopenia (ICL). The invention also relates to a method for increasing CD4-T cell activity in a HIV-infected subject by administering a compound of formula A to said subject.

The invention may be used to treat subjects at an early stage of the infection, to prevent or reduce occurrence, extent, or duration of an immunodeficiency. Typically, they can be administered immediately upon detection of an infectious disease, and prior to appearance of clinical signs. Administered very early during infection by HIV, compounds of formula A can lead the patients toward a HIV controller status. The compounds of the invention may also be administered later in infected subjects, either alone or in combination with antiviral agent(s). In such regimen, they accelerate the recovery of CD4 T lymphocytes and the restoration of their functions. Accordingly, in a particular embodiment, the invention comprises simultaneously, separately or sequentially administering to subject having a viral infection (i) an antiviral agent and (ii) a compound of formula A. Such protocol is particularly suited for treating HIV infected subjects, wherein compound A is used in combination with antiretroviral therapy (e.g., HAART), allowing to reduce HAART or even to at least temporarily interrupt HAART treatment which is known for its severe detrimental effects.

The invention also provides methods for treating cancer by increasing an immune response in the subject, comprising administering a compound of formula A to said subject. The invention also provides methods of treating CD4 T cell-linked immunodeficiency associated with cancer in a subject by administering a compound of formula A to said subject.

The duration, dosages and frequency of administering compounds or compositions of the invention may be adapted according to the subject and disease. The treatment may be used alone or in combination with other active ingredients, either simultaneously or separately or sequentially.

The compounds or compositions according to the invention may be administered in various ways or routes such as, without limitation, by systemic injection, intramuscular, intravenous, intraperitoneal, cutaneous, subcutaneous, dermic, transdermic, intrathecal, ocular (for example corneal) or rectal way, or by a topic administration on an inflammation site, and preferably by intramuscular or intravenous injection.

A typical regimen comprises a single or repeated administration of an effective amount of a compound of formula A over a period of one or several days, up to one year, and including between one week and about six months. It is understood that the dosage of a pharmaceutical compound or composition of the invention administered in vivo will be dependent upon the age, health, sex, and weight of the recipient (subject), kind of concurrent treatment, if any, frequency of treatment, and the nature of the pharmaceutical effect desired. The ranges of effectives doses provided herein are not intended to be limiting and represent preferred dose ranges. However, the most preferred dosage will be tailored to the individual subject, as is understood and determinable by one skilled in the relevant arts (see, e.g., Berkowet et al., eds., The Merck Manual, 16$^{th}$ edition, Merck and Co., Rahway, N.J., 1992; Goodmanetna., eds., Goodman and Cilman's The pharmacological Basis of Therapeutics, 10$^{th}$ edition, Pergamon Press, Inc., Elmsford, N.Y., (2001)).

Further aspects and advantages of the invention are disclosed in the following experimental section, which shall be considered as illustrative.

EXAMPLES

A. Patients and Methods

A1. Origin of the Plasma

Viremic patients (VP) included in the study had been HIV-positive for more than one year. They did not receive any antiretroviral drugs and had a viral load >10,000 RNA copies/ml with a CD4 count >200/ml at the time of blood collection (ANRS EP 33 and EP20 studies). All blood samples from VP were drawn at Hôpital Bicêtre or Centre Hospitalier de Gonesse.

A2. Production of Recombinant PLA2G1B Enzyme sPLA2G1B was produced in *E. Coli*. Inclusion bodies were solubilized in urea and afterwards renatured. sPLA2G1B was further purified by HPLC. Homogeneity of the preparations was verified by MassSpectrometry (Maldit-off). The specific activity of the enzyme was always measured and compared to standard preparations.

A3. Bioassays

Inhibition of IL-7-induced phosphorylated STAT5 nuclear translocation (NTpSTAT) was measured as follows: VP plasma (5 or 10%) was first incubated with purified HD CD4 T cells (20 min) before stimulation by IL-7 (2 nM, 15 min.). Cells were then plated on polylysine coated glass slides before fixation by PFA (1.5%) and permeabilization by methanol (90% at −20° C.). pSTAT5 was then stained by rabbit anti-STAT5 and labeled with goat anti-rabbit-Atto642. The cells were analyzed by pulsed STED microscopy and the number of nuclei expressing pSTAT5 were counted.

A4. Compounds

Compound B was bought from Selleck.

B. Results

B1. Selection of Active Compounds of Formula A

The activity of compounds of formula A towards sPLA2G1B can be tested and verified using the *E. coli* membrane assay described below:

Phospholipases A2 (PLA2s) EC 3.1.1.4 are enzymes that release fatty acids from the second carbon group of the glycerol moiety of phospholipids. The assay is based on the ability of *E. coli* membranes to incorporate exogenously added fatty acids such as oleic acid (OA). The use of radiolabelled OA allows to follow the incorporation of this fatty acid into membrane phospholipids of *E. Coli* and its release upon PLA2-mediated hydrolysis of these membranes. Preincubation of the samples, before the assay, with a specific inhibitor or a neutralizing specific antibody directed against the given sPLA2 can indicate which sPLA2 type is detected.

Preparation of Radiolabelled *E. coli* Membranes

Radiolabeled *E. coli* were prepared by the method of Franson et al (Franson R, Patriarca P, Elsbach P (1974) Phospholipid metabolism by phagocytic cells: phospholipases A2 associated with rabbit polymorphonuclear leukocyte granules. J Lipid Res 15: 380-388). An overnight culture of *E. coli* was diluted 1:20 in Luria Broth (LB) medium and incubated at 37° C. for 5 h with vigorous shaking in the presence of 1 mCi/ml [3H]OA (NET 289, NEN, 5 mCi/ml). Radiolabeled *E. coli* were then washed by incubating in fresh LB for 30 min followed by washing with 1% bovine serum albumin (BSA) to remove unincorporated radiolabel. The washed *E. coli* were autoclaved and resuspended in the appropriate amount of 0.85% saline to achieve approximately 5,000 cpm/µl. Radio-labeled *E. coli* membrane suspensions were stored at −20° C. until use. Typically, between 50-90% of the added [3H]OA was incorporated into *E. coli*.

Measurement of sPLA2 Activity

The sPLA2 assay was performed using 10 to 50 µl of the biological samples. The reaction mixtures contained 5 mM calcium chloride, 125 mM Tris HCl (pH 8.5), 2.5 mg/ml BSA, and approx. 50,000 cpm [3H]OA-labelled *E. coli* membrane suspension. Incubation periods and sample volumes are adjusted to ensure hydrolysis rates within the linear range of enzymatic assays (typically 10-20% of total substrate hydrolysis).

The reaction was carried out in a 37° C. water bath for 30 min and stopped with stop buffer containing 0.1 M EDTA and 0.2% free-fatty acids BSA. Then the tubes were centrifuged to spin down *E. Coli* membranes and aliquotes of supernatants were counted to monitor the [3H]OA released from these membranes. Total counts were also obtained by counting pellets as well as supernatant.

The sPLA2 activity (A) is calculated as follows:

$$A = A1 - A2/B \times 100.$$

A1=cpm count in 1 ml of supernatants of *E. coli* membranes after addition of the sample.

A2=cpm in the blank (1 ml supernatants of *E. coli* membranes before addition of the sample).

B=total initial cpm counts in 1 ml membranes before incubation.

A is expressed as the % hydrolysis of the total radioactivity incorporated in the *E. coli* membranes.

The results of this test allow to confirm the activity of compounds of formula A, particularly wherein X is an oxygen, and/or $R^1$ is —($CH_2$)—Ar wherein Ar is a phenyl group, and/or $R^2$ is ethyl and/or $R^3$ is —O—($CH_2$)—$COOR^4$ wherein R4 is a hydrogen atom or a methyl group. Compound B exhibits a particularly strong inhibitory effect.

B2. Specificity of Compound B

The specificity of compound B towards distinct PLA molecules is summarized in Table 1. IC50 values for a panel of secreted Phospholipase A2 (sPLA2) are shown. Compound B is able to bind sPLA2GIB as well as sPLA2GIIA, sPLA2GIID, sPLA2GIIE, sPLA2GIIF, sPLA2GV and sPLA2GX with a significant IC50. Compound B does not recognize or bind sPLA2GIII and sPLA2GXIIA.

Table 1 shows that compound B has an interesting selectivity profile with no activity towards group III PLA2. Furthermore, in plasma from HIV-infected patients, the pathogenic activity observed on CD4 lymphocytes is dominated by sPLA2GIB and we did not find any other secreted PLA2 in the 15 kDa fractions recovered from the plasma of viremic patients.

B3. Compound B Inhibits sPLA2G1B-Mediated CD4 T Cells Anergy.

Figure 2:
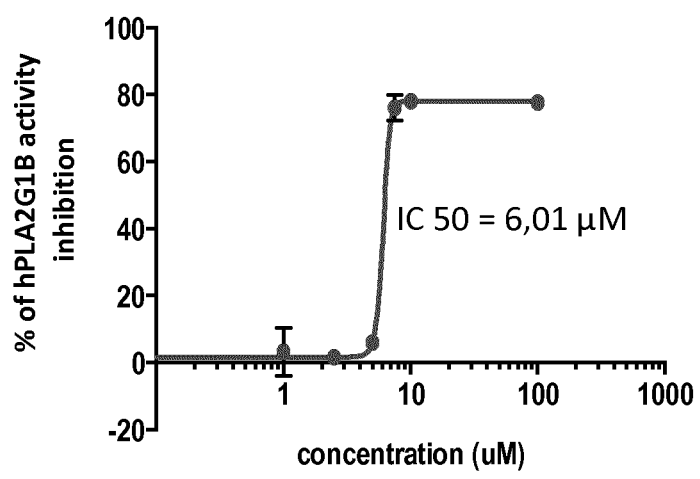
FIG. 2: Calculation of IC50 of compound B: Experimental data were analyzed by Prism software in order to precisely calculate the IC50.

We first investigated the effects of different doses of Compound B on the biological activity of recombinant sPLA2G1B as tested in the bioassay described in Materials and Methods. FIG. 1 shows that the inhibitory effects of Compound B begin at 5 microM and are maximum at 8 microM concentrations. The experiment was repeated twice. From the experimental data we derived the corresponding theoretical curve that gives the IC50. For Compound B IC 50 is 6.01 microM (FIG. 2).

We have already shown that sPLA2G1B contained in plasma of viremic patients through induction of aMMD induces a blockade of IL-7-induced nuclear translocation of phospho STAT5 (NT pSTAT5). Consequently, CD4 T lymphocytes purified from healthy donors do not respond to IL-7. Here we tested the effects of Compound B on the capacity of the sera from VP to block IL-7-induced NTp-STAT5.

Figure 3:
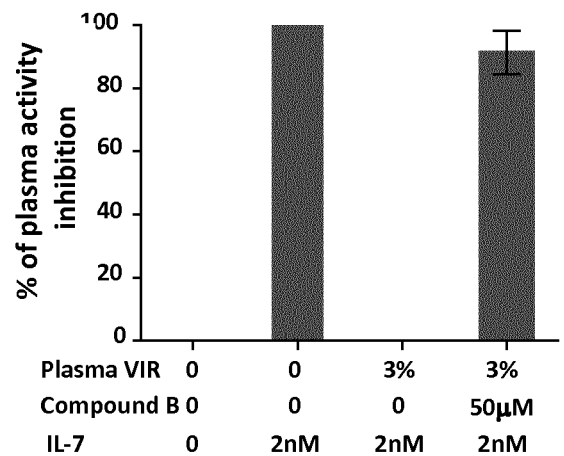
FIG. 3: Compound B restores the activity of CD4 lymphocytes: CD4 lymphocytes purified from healthy donors were exposed to sera from viremic HIV-infected patients at 3% dilution. Such exposure resulted in a complete inhibition of IL-7-induced nuclear translocation of pSTAT5. At 50 microM, compound B totally reversed this inhibition, thus restoring CD4 function. Five sera were tested and the results are given as the median +/−SD.

The effects of plasma from various HIV viremic patients (at least 5) were first titrated on the inhibition of IL-7-induced NTpSTAT5. The inhibition is measurable at 1% dilution of the plasma and the effect is maximum at 10% of the plasma. Consequently, in the experiments we used the different plasma at 3% dilution which gives between 30 to 70% of the maximum inhibition. Under these experimental conditions, we show that 50 microM Compound B (10 times its IC50) revert the inhibitory activity of the plasma (FIG. 3). It is worth noting that Compound B is even more active when contained in the plasma of the patients than against the recombinant enzyme contained in serum free buffer. The inhibition obtained with the recombinant enzyme reaches a plateau corresponding to a maximum inhibition of around 80%. By contrast, the plateau obtained when the plasma is used is around 90% inhibition, or more (compare data of FIGS. 1 and 2 with data FIG. 3). This indicates that compound B is highly active in the plasma despite the high concentration of many proteins and the presence of several lipid moieties which could interfere with sPLA2G1B and hide the access to the catalytic site after organization on multimolecular complexes of high molecular weight which could therefore impede the effects of compound B.

Figure 4:
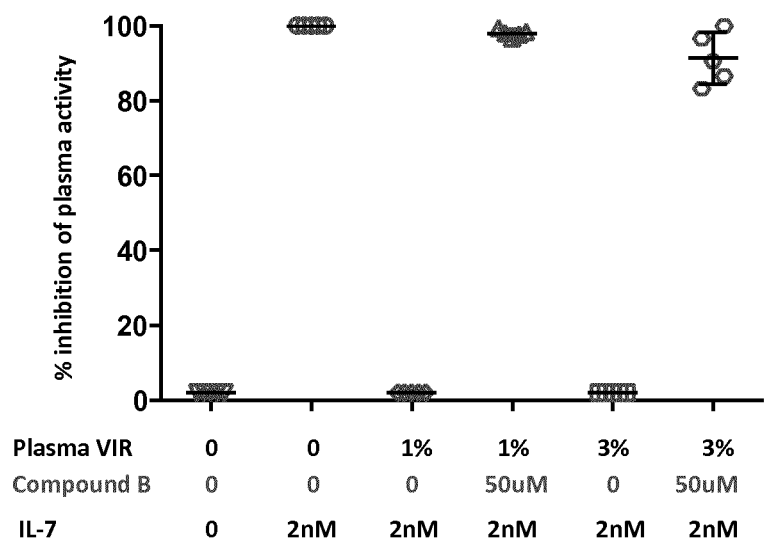
FIG. 4: Compound B restores the activity of CD4 lymphocytes: CD4 lymphocytes purified from healthy donors were exposed to sera from viremic HIV-infected patients at 1% or 3% dilution. Such exposure resulted in a complete inhibition of IL-7-induced nuclear translocation of pSTAT5. At 50 microM, compound B totally reversed this inhibition, thus restoring CD4 function.

In a further study, the plasma from 5 additional HIV-infected patients was tested. At concentrations of 1% and 3%, each of these plasma completely inhibited the effects of interleukin-7 (IL-7), as measured by the nuclear translocation of the phosphorylated transcription factor STAT5 (pSTAT5). 100% inhibition of nuclear translocation of pSTAT5 is observed (see FIG. 4). As shown in FIG. 4, Compound B at the concentration of 50 µM was able to completely reverse this inhibition and to restore normal CD4 activity. When tested on 1% plasma, the reversion is complete and when tested on 3% plasma, a very high reversion (about 90%) was also observed.

B4. Administration of Compound B to HIV-Infected Human Subjects

Compound B is administered to three groups of human subjects by injection or orally of a daily dose of 100 mg, 200 mg and 500 mg, respectively, against a placebo group. Administration is repeated during 4 months. The patients are examined at weeks 1, 2, 4, 8 and 16 for one or more of the following particular endpoints:

plasma amount of PLA2GIB: a decrease in the amount indicates an effect of compound B;

immunologic parameters of HIV infection: increase of CD4 lymphocytes/mm3, levels of CD8 lymphocytes/mm3, ratio CD4/CD8, and/or viral load (HIV RNA copy number/ml);

Toxicity marker: hepatic transaminase.

Discussion

We previously demonstrated that sPLA2G1B induces at the CD4 T lymphocyte level various defects that characterize CD4 T cells from viremic patients. We reported the inability to respond to IL-7 which explains lymphopenia. We extended this observation and demonstrated the inability of sPLA2G1B-treated CD4 lymphocytes to respond to IL-2 or to IL-4, thus explaining anergy.

Here, for the first time, we describe compounds which, through a strong inhibition of the enzymatic activity of sPLA2G1B found in the plasma of viremic HIV-infected patients, completely neutralized the pathogenic activity of the sera from all viremic patients tested. The effects observed are total, clearly pointing out to the strong potential of this therapeutic approach.

REFERENCES (1) Grossman Z, Meier-Schellersheim M, Sousa A E, Victorino R M M, Paul W E (2002) CD4+ T-cell depletion in HIV infection: are we closer to understanding the cause? *Nat Med* (4):319-323.

(2) Catalfamo M, et al. (2008) HIV infection-associated immune activation occurs by two distinct pathways that differentially affect CD4 and CD8 T cells. *PNAS* 105(50): 19851-19856.

(3) Armah K A, et al. (2012) HIV status, burden of comorbid disease and biomarkers of inflammation, altered coagulation, and monocyte activation. *Clin Infec Dis* 55(1)126-36.

The invention claimed is:

1. A method for treating a HIV-infected subject comprising administering to the subject a compound of formula A in an amount effective for restoring or stimulating CD4 T cell function in said subject,

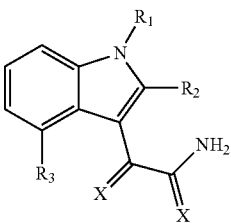

Formula A wherein:
  each X is independently an oxygen or sulfur atom;
  $R^1$ is —$(CH_2)_n$—Ar wherein n is 0, 1 or 2 and Ar is a $C_5$-$C_7$ aromatic group;
  $R^2$ is a $C_1$-$C_4$ alkyl; and
  $R^3$ is —$(O)_m$—$(CH_2)_p$—$COOR^4$ wherein m is 0 or 1; p is 0, 1, or 2; and $R^4$ is a hydrogen atom or a $C_1$-$C_3$ alkyl;
  or a salt, ester, hydrate, racemate, or enantiomer thereof.

2. The method of claim 1, wherein:
  X is an oxygen; and/or
  $R^1$ is —$(CH_2)$—Ar wherein Ar is a $C_5$-$C_7$ aromatic group; and/or
  $R^2$ is a $C_1$-$C_3$ alkyl; and/or
  $R^3$ is —O—$(CH_2)_p$—$COOR^4$ wherein p is 0, 1 or 2 and $R^4$ is a hydrogen atom or a $C_1$-$C_3$ alkyl.

3. The method of claim 1, wherein:
  X is an oxygen; and
  $R^1$ is —$(CH_2)$—Ar wherein Ar is a phenyl group; and
  $R^2$ is ethyl; and
  $R^3$ is —O—$(CH_2)$—$COOR^4$ wherein $R^4$ is a hydrogen atom or a methyl group.

4. The method of claim 1, wherein the compound is 3-(2-amino-1,2-dioxoethyl)-2-ethyl-1-(phenylmethyl)-1H-indol-4-yl)oxy)acetic acid, or a salt, ester, hydrate, racemate, or enantiomer thereof.

5. The method of claim 1, said HIV-infected subject having AIDS.

6. The method of claim 1, wherein the compound is administered to the subject at a dose comprised between 0.01 μg and 100 mg.

7. The method of claim 1, wherein the compound is administered repeatedly to the subject.

8. The method of claim 1, wherein the compound is administered by injection, by nasal, oral, mucosal, rectal administration or by inhalation.

9. The method of claim 1, wherein the compound is formulated in a pharmaceutical composition comprising a pharmaceutically acceptable carrier or excipient.

10. The method of claim 1, wherein the subject is a human subject.

* * * * *

UNITED STATES PATENT AND TRADEMARK OFFICE
CERTIFICATE OF CORRECTION

PATENT NO.         : 10,894,035 B2
APPLICATION NO.    : 15/755587
DATED              : January 19, 2021
INVENTOR(S)        : Jacques Theze and Blanche Tamarit Page 1 of 1

It is certified that error appears in the above-identified patent and that said Letters Patent is hereby corrected as shown below:

In the Specification

Column 3,
Line 57, "$(CH_2)_n$–Ar" should read -- $–(CH_2)_n–Ar$ --.
Line 60, "$(O)_m–(CH_2)_p–COOR^4$" should read -- $–(O)_m–(CH_2)_p–COOR^4$ --.

Column 10,
Line 53, "(4):319-323." should read "8(4):319-323.".

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*